US008969412B2

(12) United States Patent
Mitidieri et al.

(10) Patent No.: US 8,969,412 B2
(45) Date of Patent: Mar. 3, 2015

(54) USE FOR A COMPOSITION COMPRISING CHLOROPROCAINE HCL, A NEW COMPOSITION COMPRISING CHLOROPROCAINE HCL AND A METHOD FOR ITS MANUFACTURE

(75) Inventors: Augusto Mitidieri, Morcote (CH); Elisabetta Donati, Cavallasca (IT)

(73) Assignee: Sintetica S.A., Mendrisio (CH)

( * ) Notice: Subject to any disclaimer, the term of this patent is extended or adjusted under 35 U.S.C. 154(b) by 1233 days.

(21) Appl. No.: 11/991,449

(22) PCT Filed: Sep. 5, 2006

(86) PCT No.: PCT/EP2006/065994
§ 371 (c)(1),
(2), (4) Date: Mar. 4, 2008

(87) PCT Pub. No.: WO2007/028788
PCT Pub. Date: Mar. 15, 2007

(65) Prior Publication Data
US 2008/0306149 A1    Dec. 11, 2008

(30) Foreign Application Priority Data
Sep. 6, 2005   (IT) .............................. MI2005A1633

(51) Int. Cl.
*A61K 31/235*   (2006.01)
*A61K 31/245*   (2006.01)
*A61K 9/00*     (2006.01)

(52) U.S. Cl.
CPC ............. *A61K 31/245* (2013.01); *A61K 9/0019* (2013.01); *A61K 9/0085* (2013.01)
USPC ...................................................... 514/535

(58) Field of Classification Search
CPC .................................................... A61K 31/245
USPC ...................................................... 514/535
See application file for complete search history.

(56) References Cited

U.S. PATENT DOCUMENTS

| 4,938,970 | A | 7/1990 | Hustead et al. | 424/678 |
| 5,505,922 | A | 4/1996 | Thut et al. | 424/677 |
| 6,075,059 | A | 6/2000 | Reader | 514/738 |
| 2005/0137177 | A1 | 6/2005 | Shafer | 514/171 |

FOREIGN PATENT DOCUMENTS

| WO | WO03/017976 | 3/2003 | ............. | A61K 9/107 |
| WO | WO2004/009064 | 1/2004 | ............. | A61K 31/05 |
| WO | WO2004/058329 | 7/2004 | | |

OTHER PUBLICATIONS

Physicians' Desk Reference [50th Ed. (Medical Economics Co.), pp. 554-556; 1996].*
Niazi (Handbook of Pharmaceutical Manufacturing Formulations, Sterile Products, vol. 6, p. 150; 2004.*
Park et al. (Anesthesiology, vol. 52, No. 5, Abstract; 1980).*
Erstad (Pharmacotherapy, vol. 23, No. 9; 2003).*
Bridenbaugh et al. (Anesthesiology, vol. 25, Issue 3, pp. 372-376; 1964).*
Galinsky et al. ["Basic Pharmacokinetics and Pharmacodynamics." in: Remington: The Science and Practice of Pharmacy (Baltimore, Lippincott Williams & Wilkins, 2006), p. 1171].*
International Search Report and Written Opinion dated Feb. 12, 2007 based on PCT application No. PCT/EP06/065994.
Niesel, "Regionalanesthesie Lokalanesthesie Regionale Schmerztherapie," Georg Thieme Verlag, Stuttgart, 1994, pp. 83-86 in English translation.
Na, et al., "Spinal Chloroprocaine Solutions: Density at 37° C. and pH Titration", Anesthesia and Analgesia, 2004, vol. 98, pp. 70-74.
Yoos, et al., "Spinal 2-Chloroprocaine for Surgery: An Initial 10-Month Experience", Anesthesia and Analgesia, 2004, vol. 99, pp. 553-558.
New General Pharmaceutics (the revised third edition), NANKODO Co. Ltd, 1980, pp. 319-343.
Japanese Office Action dated May 7, 2012 for corresponding Japanese Patent Application No. 2008-529620 with English translation.
Covino, et al., "Local Anesthetics: Mechanisms of Action and Clinical Use," Grune & Stratton, New York, pp. 114-115, (1976).
Corino, "Pharmacology of Local Anaesthetic Agents," Br. J. Anaesth, 58, pp. 701-716, (1986).
Drasner, "Chloroprocaine Spinal Anesthesia: Back to the Future?," Anesth. Analg., 2005, 100, pp. 549-552.
Foldes, et al., "2-Chloroprocaine: A New Local Anesthetic Agent," Anesthesiology, 1952, 13, pp. 287-296.
Gissen, et al., "The Chloroprocaine Controversy," Regional Anesthesia, 1984, 9, pp. 135-145.
Hodgson, et al., "Procaine Compared with Lidocaine for Incidence of Transient Neurologic Symptoms," Regional Anesthesia and Pain Medicine, 2000, 25, pp. 218-222.
Pollock, "Transient Neurologic Symptoms: Etiology, Risk Factors, and Management," Regional Anesthesia and Pain Medicine, 2002, 27, pp. 581-586.
Kouri, et al., "Spinal 2-Chloroprocaine: A Comparison with Lidocaine in Volunteers," Anesth Analg., 2004, 98, pp. 75-80.
Taniguchi, et al., "Scapegoat for Chloroprocaine Neurotoxicity?," Anesthesiology, 2004, 100, 85-91.
Prithvi, *Practical Management of Pain*, (DiFazio, et al., Drugs Commonly Used for Nerve Blocking: Pharmacology of Local Anesthetics), Mosby, St. Louis (3° ed.), 2000, pp. 557-573.

(Continued)

*Primary Examiner* — Kevin E Weddington
(74) *Attorney, Agent, or Firm* — Ohlandt Greeley Ruggiero & Perle L.L.P.

(57) ABSTRACT

The present invention concerns a new use for a composition containing chloroprocaine HCl, and in particular its use for the manufacture of a drug for intrathecal narcosis. The present invention also concerns a new composition containing chloroprocaine HCl, being particularly suited to this new use, as well as a new method for manufacturing the composition.

6 Claims, No Drawings

(56) References Cited

OTHER PUBLICATIONS

Palas, "Four Years' Experience with 1% Chloroprocaine for Spinal Anesthesia in Ambulatory Anesthesia," Reg. Anesthesia Pain Med., 2005, pp. 13.

Vath et al., "Spinal 2-Chrloroprocaine: The Effect of Added Fentanyl," Anest. Analg., 98, pp. 89-93, (2004).

Wang, et al., "Chronic Neurological Deficits and Nesacaine-CE-An Effect of the Anesthetic, 2-Chloroprocaine, or the Antioxidant, Sodium Bisulfite?," Anest. Analg., 1984, 63, pp. 445-447.

Wang, et al., "Lumbar Subarachnoid Ethylenediaminetetraacetate Induces Hindlimb Tetanic Contractions in Rats: Prevention by CaC12 Pretreatment; Observation of Spinal Nerve Root Degeneration," Anest. Analg., 1992, 75, pp. 895-899.

Warren, et al., "Spinal 2-Chloroprocaine: The Effect of Added Dextrose," Anest. Analg., 2004, 98, pp. 95-101.

Winnie, et al., "Santayana's Prophecy Fulfilled," Regional Anesthesia and Pain Medicine, 2001, 26, pp. 558-564.

\* cited by examiner

USE FOR A COMPOSITION COMPRISING CHLOROPROCAINE HCL, A NEW COMPOSITION COMPRISING CHLOROPROCAINE HCL AND A METHOD FOR ITS MANUFACTURE

FIELD OF THE INVENTION

The present invention concerns the field of intrathecal anaesthesia, and in particular the provision of new compositions suited to this specific type of administration.

TECHNICAL BACKGROUND

Given the current trend in medicine—dictated by the requirement of national health services and private insurance companies to limit medication costs—for carrying out the greatest possible number of surgical operations without general anaesthetic and therefore without patient hospitalisation, there is current interest in further developing local and regional, rather than general, anaesthetic is techniques. Given recent developments and the comparative progress achieved, regional and local anaesthesias prove to be even safer than general anaesthesia, which is hence avoided particularly in vulnerable patients such as the elderly. It is therefore a problem not only of cost to be borne by the community, but also above all of improving the quality of therapy offered to the patient, which improves compliance thereof.

The aforementioned so-called regional anaesthesias include, as a rule, techniques suitable for administering local anaesthetics to the spine and the nerve plexus of the upper extremities, as well as to the individual peripheral nerves. Spinal techniques are divided in their turn into epidural injection and intrathecal injection (whereby the narcotic is injected into the so-called subarachnoid space) which are both suitable for inducing, by means of a targeted anaesthetic injection into a contained spinal space, a regional anaesthesia of the lower extremities by temporarily interrupting the nervous connection between said extremities and the brain. While the intrathecal technique is more invasive than the epidural technique (in that the injection is carried out in a region deeper within the spine), it has the advantage of requiring comparatively small quantities of the anaesthetic used.

An ideal intrathecal anaesthetic for outpatient surgery use should give an immediate or at least a rapid effect (and thus have a brief induction period—so called onset time), should have an easily adjustable action for a predictable duration, and should exhibit low neurotoxicity as well as be without side effects. A narcotic already in use for intrathecal anaesthesia is procaine, which can however result in an inadequacy rate of 17% (1). Instead, lidocaine has been associated with symptoms of so-called transient neurologic syndrome (TNS) (2), whereas bupivacaine though efficient, can nevertheless induce blocks whose duration in some cases is hard to predict despite low dose administration.

It therefore appears that none of the anaesthetics currently used for intrathecal application, in currently authorized formulations, fully satisfies all the criteria that characterize an ideal preparation. The need remains therefore to provide additional and improved compositions for intrathecal administration.

SUMMARY

In attempting to resolve the aforesaid problems, the inventors of the present Application have surprisingly found that the previously described problems of the known art can be overcome by using a preservative-free composition comprising chloroprocaine HCl in solution in water for injection, for the manufacture of a drug for intrathecal narcosis.

The inventors of the present invention have also found a method for the manufacture of a drug useful for intrathecal narcosis, characterized by using a preservative-free composition comprising chloroprocaine HCl in solution in water for injection. Furthermore, the inventors of the present Application have found a new pharmaceutical composition in the form of an aqueous solution, proven to be particularly suited for intrathecal administration, consisting, per ml of solution in water for injection, of the following substances: 9.0-11 mg chloroprocaine HCl, 6-8 mg NaCl, and HCl in a sufficient quantity to impart a pH of 3.0-4.0. The inventors of the present Application have also found a method for obtaining a pharmaceutical composition as aforedescribed comprising the following steps:

mixing water for injection, chloroprocaine HCl, NaCl and HCl in the necessary quantities, in an inert gas atmosphere to give a medicated solution under inert gas, filtering the medicated solution through a sterilizing filter (0.22 µm), dispensing the filtered medicated solution into vials under inert gas, sterilizing the filtered medicated solution in sealed vials under inert gas at at least 121° C. for at least 10 minutes ($F_0$>10 minutes), to provide a sterilized medicated solution.

DETAILED DESCRIPTION OF THE INVENTION

Chloroprocaine, or 2-(diethylaminoethyl)-4-amino-chlorobenzoate (CAS 3858-89-7), in its hydrochloride addition salt form (chloroprocaine HCl) is a long-known narcotic substance, having been used for over 50 years. Chloroprocaine (HCl) has a similar pharmacological profile to lidocaine, with a brief onset time (15-20 minutes) and a short duration (30-60 minutes) (3). Chloroprocaine is rapidly metabolised; indeed, its plasma half-life is between 45 and 60 seconds, making it the most rapidly metabolised anaesthetic in clinical use known today (4, 5). Given this characteristic, chloroprocaine has a very low systemic toxicity. Chloroprocaine is also used as a local anaesthetic in outpatient surgery when a very brief anaesthesia is required (3,6).

Despite all these apparent advantages chloroprocaine, and in particular chloroprocaine HCl, in its currently available formulations ["Chloroprocaine Hydrochloride Injection, USP" of Bedford Laboratories (Boehringer Ingelheim) and Nesacaine®-MPF of AstraZeneca] is authorized, for example by the FDA and Swiss Medic, exclusively for epidural but not for intrathecal application. In this respect, with the aim of preventing as far as possible either involuntary or accidental off-label usage of these preparations, the information leaflets of the respective commercial products give specific warnings that explicitly advise against intrathecal use thereof. As a result chloroprocaine HCl is not currently used for intrathecal anaesthesia, neither are there formulations suitable and authorised for this type of administration on the world market at present. An object of the present invention is therefore to overcome the problems of the known art and to allow intrathecal administration of chloroprocaine HCl, preferably by providing new formulations suitable for this application. This is because all previously developed formulations, despite the several attempts described in the literature, have so far proved to be unsuitable for allowing safe intrathecal use of chloroprocaine HCl.

Although the intrathecal administration of chloroprocaine HCl was initially proposed—in view of its very fast hydrolysis by pseudocholinesterase—almost immediately after its appearance in clinical anaesthesia by Foldes and McNall (7), this path (which was never actually embarked on in the sense that it never led to the development of specific formulations) was then rapidly abandoned in the light of a some serious incidents following cases of accidental intrathecal administration during "normal" epidural administration of the preparation available at that time, namely, Nesacaine®-CE (8). Specifically, in the cases in question, lower limb paralysis and sacral neurological dysfunction occurred whose complete resolution was achieved in up to 6-12 weeks and was actually found to be permanent in some cases. Although in some subsequent studies it was suggested that the low pH and/or the presence of preservative (sodium bisulfite) in Nesacaine®-CE was responsible for the disorders found (9,10), and although in the mid 90's other is preservatives were also removed from formulations available commercially at that time, such as EDTA (11), the whole picture, in spite of off-label experiments recently conducted with new formulations including Nesacaine®-MPF (12, 13, 14, 15), is still far from clear, in that another work published in the same period (16) actually attributes strong neuroprotective properties to specifically bisulfite, precisely putting the use of modern formulations into question since they lack this excipient. Although these further developments have led to discussions and controversies (17), the current situation is that the existing preservative-free formulations (as likewise those containing the antioxidant sodium bisulfite, which still remain on the market) are not authorised for intrathecal use, and above all that no formulation specific for this type of administration has ever been developed. This is because, given past experiences, and despite recent developments that attributed side effects to the presence of bisulfite and/or the acid environment, which were in turn proved wrong, chloroprocaine HCl is still considered unsuitable for intrathecal administration, in that from the current state of studies conducted it emerges overall that:

all the neurotoxicological disorders that took place were indeed linked to this type of administration, being apparently particularly problematic the pH of commercial chloroprocaine HCl solutions is in any case distinctly lower than that of solutions of other anaesthetics and could therefore have contributed to the problems that arose.

The inventors of the present Application have now surprisingly found that the aforedescribed problems of the known art can be overcome by the use of a preservative-free composition comprising chloroprocaine HCl in solution in water for injection, and, in particular, free of sodium bisulfate, for the manufacture of a drug for intrathecal narcosis. In accordance with a particularly preferred embodiment, a pharmaceutical composition suitable for intrathecal administration is provided in the form of an aqueous solution, consisting, per ml of solution in water for injection, of the following substances: 9.0-11 mg chloroprocaine HCl, 6-8 mg NaCl and HCl in a sufficient quantity to impart a pH of 3.0 to 4.0.

In accordance with a particularly preferred embodiment, the components of the composition of the present invention are balanced to fall within the aforesaid parameters, until an osmolality of between 270 and 300 mOsm/kg is achieved.

In accordance with another particularly preferred embodiment, the components of the composition of the present invention are balanced to fall within the aforesaid parameters, until a relative density at 20° C. of between 1.0070 and 1.0080 is achieved.

Preferably, the new pharmaceutical composition provided by the inventors of the present invention is produced in accordance with a new method established by the inventors and comprises the following steps:

mixing water for injection, chloroprocaine HCl, NaCl and HCl, in the necessary quantities, in an inert gas atmosphere to give a medicated solution, still under inert gas, filtering the medicated solution through a sterilizing filter (0.22 μm), dispensing, under inert gas, the filtered medicated solution into vials, sterilizing the filtered medicated solution under inert gas, in the sealed vials, at at least 121° C. for at least 10 minutes ($F_0 > 10$ minutes), to provide a sterilized medicated solution.

Preferably, the inert gas is chosen from the group consisting of nitrogen and a rare gas. The purging step with inert gas is particularly critical and must guarantee the lowest possible oxygen residue with the aim of maintaining the active principle stable for a long period of time (up to 5 years under ordinary storage conditions). Preferably, dispensing is done into 5 ml vials. The vials can be of clear glass, given the high stability of the specific solutions provided by the present invention. In addition to enabling preservatives, particularly antioxidants, to be omitted, the method established by the inventors also allows more effective results to be attained, from the sterilization viewpoint, than achieved by aseptic production (by sterilizing filtration), currently used for compositions of the known art.

As previously seen, nitrogen is applied to the medicated solution during all the production steps, starting from degassing of the water for injection, right up to sealing of the vials. In conclusion it has been shown that the present invention allows the use of a preservative-free composition comprising chloroprocaine HCl in solution in water for injection for the manufacture of a drug for intrathecal narcosis, and in particular that the new compositions developed by the inventors of the present Application resolve the aforementioned problems.

CITED LITERATURE (1) Hodgson, P S, Liu S S, Batra M S et al. Procaine compared with lidocaine for incidence of transient neurologic symptoms. Reg. Anesth. Pain Med, 2000; 25: 218-22.

(2) Pollock J E. Transient neurologic symptoms: etiology, risk factors, and managements. Reg. Anesth. Pain Med. 2002; 27: 581-6.

(3) Niesel H C H, Regionalanästhesie Lokalanästhesie Regionale Schmerztherapie; G. Thieme Verlag, Stuttgart, 1994; 83-86.

(4) Prithvi Raj P. Practical Management of Pain, Mosby, St. Louis (3° ed.), 2000; 557-572.

(5) Covino B G and Vassallo H G. Local anesthetics: Mechanisms of Action and Clinical Use, Grune & Stratton, N. York, 1976; 114-115.

(6) Covino B G. Pharmacology of local anesthetic agents, Br. J. Anaesth, 1986; 58: 701-716.

(7) Foldes F F and McNall P G. 2-Chloroprocaine: a new local anesthetic agent; Anesthesiology, 1952; 13: 287-96.

(8) Winnie A P, Nader A M. Santayana's prophecy fulfilled. Reg. Anesth. Pain Med. 2001; 26: 558-64.

(9) Wang B C, Hillmann D E, Spielhoz N I et al. Chronic neurological deficits and Nesacaine—CE an effect of the anesthetic, 2-chloroprocaine, or the antioxidant, sodium bisulfite? Anesth Analg. 1984; 63: 445-7.

(10) Gissen A J, Datta S, Lambert D. The chloroprocaine controversy. Reg. anesth. 1984; 9: 124-45.
(11) Wang B C, Li D, Hiller J M et al. Lumbar subarachnoid ethylenediamine tetraacetate induces hind limb tetanic contractions in rats: prevention by $CaCl_2$ pretreatment; observation of spinal nerve root degeneration, Anesth Analg. 1992; 75: 895-899.
(12) Vath J S and Kopacz D J. Spinal 2-chloroprocaine: the effect of added fentanyl, Anesth. Analg. 2004; 98: 81-88.
(13) Palas T A R. Two years experience with 1% chloroprocaine for spinal anesthesia in ambulatory anesthesia, Society for Ambulatory Anesthesia, annual Meeting 2003, Syllabus, P-29.
(14) Kouri M E and Kopacz D J. Spinal 2-chloroprocaine: a comparison with lidocaine in volunteers, Anesth Analg 2004; 98: 75-80.
(15) Warren D T and Kopacz D J. Spinal 2-chloroprocaine: the effect of added dextrose, Anesth Analg. 2004; 98: 95-101.
(16) Taniguchi M, Bollen A W and Drasner K. Sodium bisulfite. Scapegoat for chloroprocaine neurotoxicity? Anesthesiology 2004; 100: 85-91.
(17): Drasner, Kenneth: "Chloroprocaine Spinal Anesthesia: Back to the Future?" Anesth. Analg. 2005; 100: 549-52.

The invention claimed is:

1. A method for inducing a regional anaesthesia to a subject in need thereof which comprises the intrathechal administration of a composition consisting essentially of, per ml of solution in water for injection, the following substances:
9-11 mg chloroprocaine HCl;
6-8 mg NaCl;
HCl in a sufficient quantity to impart a pH of 3.0-4.0; and
water for injection,
wherein the composition is a preservative-free composition.

2. The method as claimed in claim 1, wherein the composition has an osmolality of between 270 and 300 mOsm/kg.

3. The method as claimed in claim 1, wherein the composition has a relative density at 20° C. of between 1.0070 and 1.0080.

4. A pharmaceutical composition for inducing a regional anaesthesia by intrathechal administration in the form of an aqueous solution consisting essentially of, per ml of solution in water for injection, the following substances:
9-11 mg chloroprocaine HCl,
6-8 mg NaCl,
HCl in a sufficient quantity to impart a pH of 3.0-4.0, and
water for injection,
wherein the composition is a preservative-free composition.

5. The composition as claimed in claim 4, wherein the composition has an osmolality of between 270 and 300 mOsm/kg.

6. The composition as claimed in claim 4, wherein the composition has a relative density at 20° C. of between 1.0070 and 1.0080.

* * * * *